United States Patent [19]
Demmering et al.

[11] Patent Number: 5,455,370
[45] Date of Patent: Oct. 3, 1995

[54] PROCESS FOR THE PRODUCTION OF FATTY ACID LOWER ALKYL ESTERS

[75] Inventors: Guenther Demmering, Solingen; Christian Pelzer, Linnich; Lothar Friesenhagen, Duesseldorf, all of Germany

[73] Assignee: Henkel Kommanditgesellschaft auf Aktien, Duesseldorf, Germany

[21] Appl. No.: 178,281

[22] PCT Filed: Jun. 29, 1992

[86] PCT No.: PCT/EP92/01463

§ 371 Date: Jan. 10, 1994

§ 102(e) Date: Jan. 10, 1994

[87] PCT Pub. No.: WO93/01263

PCT Pub. Date: Jan. 21, 1993

[30] Foreign Application Priority Data

Jul. 8, 1991 [DE] Germany .................... 41 22 530.9

[51] Int. Cl.$^6$ .................................................. C11C 3/00
[52] U.S. Cl. ........................................................ 554/169
[58] Field of Search ............................................ 554/169

[56] References Cited

U.S. PATENT DOCUMENTS 2,727,049  12/1955  Braconier et al. ............... 260/410.9
4,608,202  8/1986   Lepper et al. ................... 260/410.9

FOREIGN PATENT DOCUMENTS 0127104   12/1984  European Pat. Off. .
0198243   10/1986  European Pat. Off. .
2824782   12/1978  Germany .
53-006161  3/1978  Japan .
712747     7/1954  United Kingdom .

*Primary Examiner*—José G. Dees
*Assistant Examiner*—Deborah D. Carr
*Attorney, Agent, or Firm*—Wayne C. Jaeschke; Norvell E. Wisdom, Jr.; Daniel S. Ortiz

[57] ABSTRACT

Fatty acid glycerides can be transesterified with lower aliphatic alcohols if the reaction is carried out in the presence of fatty acids corresponding to formula (II):

$$R^2\text{—COOH} \qquad (II),$$

in which $R^2$ is an aliphatic hydrocarbon moiety containing 11 to 17 carbon atoms and 0, 1 or 2 double bonds. The products are distinguished by a low content of bound glycerol and a low acid value. Removal or neutralization of the catalyst is unnecessary because, after the transesterification, the fatty acids are also present in the form of their esters.

23 Claims, No Drawings

PROCESS FOR THE PRODUCTION OF FATTY ACID LOWER ALKYL ESTERS

This application is a 371 of PCT/EP 92/01463 filed Jun. 29, 1992.

FIELD OF THE INVENTION

This invention relates to a process for the production of fatty acid lower alkyl esters by transesterification of fatty acid glycerides with lower aliphatic alcohols in the presence of free fatty acids.

PRIOR ART

Fatty acid methyl esters are important industrial raw materials for the production of a number of products, for example lubricants and surfactants. The esters are normally produced from natural fats and oils, i.e. full or partial esters of glycerol with fatty acids, which are transesterified with methanol in the presence of catalysts. Processes for the transesterification of fats and oils are described in a number of publications. The synoptic article in Seifen-Ole-Fette-Wachse, 114, 595 (1988) is cited here as representative of those publications.

If the transesterification is to be carried out with satisfactory conversions in an economically worthwhile time, catalysts have to be used. Suitable catalysts are, in particular, heavy metal compounds, such as for example zinc oxide [GB 712,747] and zinc silicate [U.S. Pat. No. 2,727,049]. However, processes of this type are attended by the disadvantage that, for toxicological reasons, the catalysts cannot remain in the product after transesterification, but instead have to be removed at considerable cost.

The transesterification may also be carried out in the presence of mineral acids which merely have to be neutralized on completion of the reaction. Although the problem of removal does not arise in this case, the volume/time yields of transesterification products are distinctly poorer by comparison with heavy metal catalysis; this is an obstacle to industrial application of the process.

Accordingly, the problem addressed by the present invention was to provide a process for the transesterification of fatty acid glycerides which would be free from the disadvantages mentioned above.

DESCRIPTION OF THE INVENTION

This invention relates to a process for the production of fatty acid lower alkyl esters by transesterification of fatty acid glycerides in the presence of acidic catalysts, characterized in that full and/or partial esters of glycerol with fatty acids corresponding to formula (I):

$$R^1\text{—COOH} \qquad (I),$$

in which $R^1$ is an aliphatic hydrocarbon moiety containing 5 to 23 carbon atoms and 0 or 1 to 5 double bonds, are reacted with lower aliphatic alcohols containing 1 to 4 carbon atoms at elevated temperature and, optionally, elevated pressure in the presence of at least one fatty acid corresponding to formula (II):

$$R^2\text{—COOH} \qquad (II),$$

in which $R^2$ is an aliphatic hydrocarbon radical containing 11 to 17 carbon atoms and 0, 1 or 2 double bonds.

It has surprisingly been found that the transesterification of fatty acid glycerides in the presence of fatty acids leads to volume/time yields of transesterification products which, hitherto, could only be achieved in the presence of heavy metal compounds. Another advantage of the process according to the invention is that, on completion of the transesterification, the fatty acid is also present as an ester so that there is no need for removal or neutralization of the catalyst. In addition, production stoppages attributable to catalyst deposits can be reduced and contamination of the glycerol released and of the wastewater by heavy metal traces can be avoided.

Suitable starting materials for transesterification by the process according to the invention are both full esters and partial esters of glycerol with fatty acids; triglycerides are preferably used. Typical examples are glycerol esters of caproic acid, caprylic acid, capric acid, lauric acid, myristic acid, palmitic acid, palmitoleic acid, stearic acid, oleic acid, elaidic acid, petroselic acid, linoleic acid, linolenic acid, chaulmoogric acid, ricinoleic acid, arachic acid, gadoleic acid, behenic acid, erucic acid, arachidonic acid and clupanodonic acid.

The glycerol esters of the fatty acids mentioned above may be both synthetic and natural products, particularly those in which the glycerol is attached to two or three different fatty acids. Natural glycerol fatty acid esters are understood to be fats and oils of animal or vegetable origin, for example coconut oil, palm oil, palm kernel oil, peanut oil, cottonseed oil, rapeseed oil, sunflower oil, coriander oil, linseed oil, soybean oil, beef tallow or fish oil.

The natural fatty acid glycerides may be used for the transesterification without any further pretreatment. However, it is advisable to subject the starting materials beforehand to a treatment with bleaching earth ("fuller's earth") in order to facilitate the removal of husk remains and mucilaginous substances.

Lower aliphatic alcohols suitable for replacing the glycerol in the fatty acid ester are ethanol, n-propyl alcohol, i-propyl alcohol, n-butanol or tert-butanol. The transesterification is preferably carried out with methanol.

Typical examples of fatty acids corresponding to formula (II) which catalyze the transesterification of the fatty acid glycerides in the process according to the invention are lauric acid, myristic acid, palmitic acid, stearic acid, oleic acid and linoleic acid.

As usual in oleochemistry, these fatty acids may also be present in the form of technical cuts of the type obtained in the pressure hydrogenation of natural fats and oils, for example palm oil, palm kernel oil, coconut oil or beef tallow. It is preferred to use technical coconut oil fatty acids, technical palm kernel oil fatty acids, technical oleic acid and mixtures thereof.

The quantity of fatty acids corresponding to formula (II) which are added to the glycerides as catalyst is determined by the acid value of the starting products. It has proved to be optimal to adjust the reaction mixture containing the glyceride and the alcohol to an acid value of 10 to 30, preferably 15 to 20 and, more preferably, 18 to 19 by addition of free fatty acids. If the mixtures have lower acid values, unsatisfactory yields are obtained in the transesterification. If the acid value of the reaction mixture is too high, the transesterified product will contain free, non-esterified fatty acids which have to be subsequently neutralized.

If untreated fatty acid glycerides having acid values below 10 are used instead of de-acidified oils, the quantity of fatty acid used in the process according to the invention will have to be selected so that a total acid value of 10 to 30 is established in the reaction mixture. The quantity of catalytically active fatty acid corresponding to formula (II) is normally between 1 and 20% by weight, preferably between 2 and 15% by weight and, more preferably, between 3 and 10% by weight, based on the fatty acid glyceride.

The fatty acids corresponding to formula (II) may be added to one of the two starting materials—fatty acid glyceride or alcohol—or to a mixture thereof, for example by stirring at optionally elevated temperature. The transesterification may be carried out in known manner at elevated temperature and, optionally, elevated pressure, for example at temperatures of 150° to 300° C. and, more particularly, 200° to 250° C. and under pressures of 1 to 100 bar and, more particularly, 50 to 80 bar. The transesterification may be followed by working up in which the glycerol released and residues of unreacted alcohol are removed and the fatty acid lower alkyl ester obtained is distilled or fractionated.

The following Examples are intended to illustrate the invention without limiting it in any way.

EXAMPLES

EXAMPLE 1

320 g (0.5 moles) of refined coconut oil having the following fatty acid composition:

| | |
|---|---|
| Caproic acid | 0.5% by weight |
| Caprylic acid | 8% by weight |
| Capric acid | 7% by weight |
| Lauric acid | 48% by weight |
| Myristic acid | 17% by weight |
| Palmitic acid | 9% by weight |
| Stearic acid | 2% by weight |
| Oleic acid | 7% by weight |
| Linoleic acid | 1.5% by weight |
| Acid value | 0.3 | and 320 g (10 moles) of methanol (ratio by volume 1:1) were introduced into a 1 liter autoclave and 58 g—corresponding to 9 % by weight, based on the starting products of technical oleic acid (average molecular weight 281 ) were subsequently added. The following characteristics were determined for the mixture:

| | |
|---|---|
| Bound glycerol | 13.8% by weight |
| Acid value | 18 |

The reaction mixture was then kept at a temperature of 240° C. and under a pressure of 65 bar for 180 minutes. After cooling and venting of the autoclave, a transesterification product with the following characteristics was obtained:

| | |
|---|---|
| Bound glycerol | 1.2% by weight |
| Acid value | 0.8. |

EXAMPLE 2

Example 1 was repeated with 320 g of unrefined coconut oil (acid value: 9.0) pretreated with bleaching earth and active carbon in a ratio by weight of 1:1 and 320 g of methanol. On this occasion, a technical $C_{12/18}$ fatty acid (average molecular weight 200) based on coconut oil/palm kernel oil (1:1) was used as the transesterification catalyst in a quantity of 20.5 g, corresponding to 3% by weight based on the starting products.

| | |
|---|---|
| Bound glycerol (before transesterification) | 13.8% by weight |
| Acid value (before transesterification) | 18 |
| Bound glycerol (after transesterification) | 1.0% by weight |
| Acid value (after transesterification) | 0.8 |

EXAMPLE 3

Example 1 was repeated with 320 g (0.5 mole) of unrefined palm kernel oil having the following fatty acid composition:

| | |
|---|---|
| Caproic acid | 0.5% by weight |
| Caprylic acid | 4% by weight |
| Capric acid | 5% by weight |
| Lauric acid | 51% by weight |
| Myristic acid | 15% by weight |
| Palmitic acid | 7% by weight |
| Stearic acid | 2% by weight |
| Oleic acid | 15% by weight |
| Linoleic acid | 0.5% by weight |
| Acid value | 0.8 | which had been pretreated with bleaching earth and active carbon in a ratio by weight of 1:1, and 320 g of methanol. On this occasion, a mixture of a technical $C_{12/18}$ fatty acid (average molecular weight 200) and a technical oleic acid (average molecular weight 281 ) in a ratio by weight of 1:1 was used as the transesterification catalyst in a quantity of 47 g, corresponding to 7.3 % by weight based on the starting products.

| | |
|---|---|
| Bound glycerol (before transesterification) | 13.2% by weight |
| Acid value (before transesterification) | 18 |
| Bound glycerol (after transesterification) | 1.4% by weight |
| Acid value (after transesterification) | 1.1. |

EXAMPLE 4

The transesterification was carried out continuously in an apparatus of the following construction:

From intake vessels for the methanol and the oil/fatty acid mixture, the starting materials were continuously pumped into the reactor via a preheating stage. After transesterification, the crude reaction mixture was cooled and transported through a pressure separator and a pressure-retaining valve into an expansion vessel.

In the reactor, a mixture of 5,000 g (7.8 moles) of refined coconut oil having the following fatty acid composition:

| | |
|---|---|
| Caproic acid | 0.5% by weight |
| Caprylic acid | 8% by weight |
| Capric acid | 7% by weight |
| Lauric acid | 48% by weight |
| Myristic acid | 17% by weight |
| Palmitic acid | 9% by weight |
| Stearic acid | 2% by weight |
| Oleic acid | 7% by weight |
| Linoleic acid | 1.5% by weight |
| Acid value | 0.3 | and 450 g—corresponding to 9% by weight—of a technical $C_{12/18}$ coconut oil fatty acid (average molecular weight 200) was reacted with methanol in a ratio by volume of 1:1.3. The throughput of oil/fatty acid was 0.9 l/h while the throughput of methanol was 1.2 l/h.

After a reaction time of about 70 mins at a temperature of 240° C. and a pressure of 9 bar, the transesterification mixture was obtained in the form of a two-phase product after cooling and venting.

| | |
|---|---|
| Bound glycerol (before transesterification) | 13.8% by weight |
| Acid value (before transesterification) | 18 |
| Bound glycerol (after transesterification) | 1.4% by weight |
| Acid value (after transesterification) | 1.5 |

We claim:

1. A process for the production of fatty acid lower alkyl esters, which comprises:
   a) forming a mixture comprising at least one lower aliphatic $C_{1-4}$ alcohol, a fatty acid corresponding to formula (II):

$$R^2\text{—COOH} \qquad \text{(II),}$$

in which $R^2$ is an aliphatic hydrocarbon moiety containing 11 to 17 carbon atoms and 0, 1 or 2 double bonds, as a sole acidic catalyst and full, partial, or both full and partial esters of glycerol with fatty acids corresponding to formula (I):

$$R^1\text{—COOH} \qquad \text{(I),}$$

in which $R^1$ is an aliphatic hydrocarbon moiety containing 5 to 23 carbon atoms and 0 or 1 to 5 double bonds, said fatty acid of the formula (II) being present in a quantity that an acid value of 10 to 30 is established in the mixture, based on the mixture as a whole, and b) transesterifying the glycerol esters in the mixture with the lower aliphatic $C_{1-4}$ alcohols at an elevated temperature and optionally under elevated pressure.

2. A process as claimed in claim 1, wherein methanol is used as the lower aliphatic alcohol.

3. A process as claimed in claim 2, wherein the mixture comprises triglycerides of the fatty acids corresponding to Formula (I).

4. A process as claimed in claim 3, wherein the fatty acids corresponding to formula (II) are used in quantities of 1 to 20% by weight, based on the fatty acid glyceride in the mixture.

5. A process as claimed in claim 4, wherein the transesterification is carried out at temperatures of 150° to 300° C.

6. A process as claimed in claim 5, wherein the transesterification is carried out under pressures of 1 to 100 bar.

7. A process as claimed in claim 1, wherein the mixture comprises triglycerides of the fatty acids corresponding to formula (1).

8. A process as claimed in claim 7, wherein the mixture comprises the fatty acids corresponding to Formula (11) in quantities of 1 to 20% by weight, based on the fatty acid glyceride in the mixture.

9. A process as claimed in claim 2, wherein the mixture comprises fatty acids corresponding to formula (II) in quantities of 1 to 20% by weight, based on the fatty acid glyceride in the mixture.

10. A process as claimed in claim 1, wherein the mixture comprises fatty acids corresponding to formula (II) in quantities of 1 to 20% by weight, based on the fatty acid glyceride in the mixture.

11. A process as claimed in claim 10, wherein the transesterification is carried out at temperatures of 150° to 300° C.

12. A process as claimed in claim 9, wherein the transesterification is carried out at temperatures of 150° to 300° C.

13. A process as claimed in claim 8, wherein the transesterification is carried out at temperatures of 150° to 300° C.

14. A process as claimed in claim 7, wherein the transesterification is carried out at temperatures of 150° to 300° C.

15. A process as claimed in claim 3, wherein the transesterification is carried out at temperatures of 150° to 300° C.

16. A process as claimed in claim 2, wherein the transesterification is carried out at temperatures of 150° to 300° C.

17. A process as claimed in claim 1, wherein the transesterification is carried out at temperatures of 150° to 300° C.

18. A process as claimed in claim 4, wherein the transesterification is carried out under pressures of 1 to 100 bar.

19. A process as claimed in claim 3, wherein the transesterification is carried out under pressures of 1 to 100 bar.

20. A process as claimed in claim 1, wherein the transesterification is carried out under pressures of 1 to 100 bar.

21. The process of claim 1 wherein the acid value of the mixture is from 15 to 20.

22. The process of claim 2 wherein the acid value of the mixture is 15 to 20.

23. The process of claim 22 wherein the transesterification is carried out at a temperature of 150° to 300° C.

* * * * *